US005462215A

United States Patent [19]
Viola et al.

[11] Patent Number: 5,462,215
[45] Date of Patent: Oct. 31, 1995

[54] LOCKING DEVICE FOR AN APPARATUS FOR APPLYING SURGICAL FASTENERS

[75] Inventors: Frank J. Viola, Sandy Hook; David T. Green, Westport; Henry Bolanos, East Norwalk, all of Conn.

[73] Assignee: United States Surgical Corporation, Norwalk, Conn.

[21] Appl. No.: 352,976

[22] Filed: Dec. 9, 1994

Related U.S. Application Data

[63] Continuation of Ser. No. 275,227, Jul. 14, 1994, abandoned, which is a continuation of Ser. No. 71,935, Jun. 3, 1993, abandoned, which is a continuation of Ser. No. 780,861, Oct. 18, 1991, abandoned.

[51] Int. Cl.$^6$ .................................................. A61B 17/068
[52] U.S. Cl. .................................. 227/176; 227/8; 227/19
[58] Field of Search ................................ 227/8, 19, 176, 227/177, 178, 182

[56] References Cited

U.S. PATENT DOCUMENTS

| | | |
|---|---|---|
| D. 283,733 | 5/1986 | Rawson et al. . |
| D. 322,143 | 12/1991 | Spreckelmeier . |
| 2,174,219 | 9/1939 | Balma . |
| 2,246,647 | 6/1941 | Vancura . |
| 3,079,606 | 3/1963 | Bobrov et al. . |
| 3,490,675 | 1/1970 | Green et al. . |
| 3,494,533 | 2/1970 | Green et al. . |
| 3,499,591 | 3/1970 | Green . |
| 3,675,688 | 7/1972 | Bryan et al. . |
| 3,692,224 | 9/1972 | Astafiev et al. . |
| 3,735,762 | 5/1973 | Bryan et al. . |
| 3,795,034 | 3/1974 | Strekopytrov et al. . |
| 3,844,289 | 10/1974 | Noiles . |
| 3,873,016 | 3/1975 | Fishbein . |
| 4,006,786 | 2/1977 | Speicher ........................................ 227/8 |
| 4,086,926 | 5/1978 | Green et al. . |
| 4,108,306 | 8/1978 | Samuels et al. . |

(List continued on next page.)

FOREIGN PATENT DOCUMENTS

| | | |
|---|---|---|
| 54765 | 9/1986 | Australia . |
| 54764 | 9/1986 | Australia . |
| 0324638 | 7/1989 | European Pat. Off. . |
| 0373762 | 6/1990 | European Pat. Off. . |
| 0380025 | 8/1990 | European Pat. Off. . |
| 0489436 | 6/1992 | European Pat. Off. . |
| 0514139 | 11/1992 | European Pat. Off. . |
| 7037682 | 5/1972 | France . |
| 2744824 | 4/1978 | Germany . |
| 2070499 | 9/1981 | United Kingdom . |
| 8302247 | 7/1983 | WIPO . |

OTHER PUBLICATIONS

"Disposable EEA Surgical Stapler and Curved Disposable EEA Surgical Stapler", Information Booklet, printed Jan. 1985.
Anderson et al., Surgical Stapling, "Thoraci, Vascular and Esophageal Procedures", pp. 1–101, 1988.
Brolin et al., Surgical Stapling, "Bariatric Procedures for Morbid Obesity", pp. 1–115, 1989.
Flickinger et al., Surgical Stapling, "Gastric and Small Bowel Procedures", pp. 1–145, 1988.
"Auto Suture® Premium Poly CS™–57 Disposable Surgical Stapler," printed 1986, reprinted 1990.
"Auto Suture® Poly CS™–57 Disposable Surgical Stapler", printed Jul. 1988.
"Auto Suture® Poly CS™–57 Disposable Loading Units with Lactomer® Absorbable Copolymer Staples", printed Jul. 1988.

*Primary Examiner*—Scott A. Smith

[57] ABSTRACT

A locking device for a surgical stapling or fastening instrument for applying surgical fasteners to tissue. The locking device is positioned on the jaw mechanism of the fastening instrument and engages a cartridge when the cartridge includes fasteners, and pivots through the cartridge after the fasteners have been fired to prevent the cartridge carrying jaw from being approximated into a firing position when the cartridge is empty.

29 Claims, 5 Drawing Sheets

U.S. PATENT DOCUMENTS

| | | | |
|---|---|---|---|
| 4,202,479 | 5/1980 | Razgulov et al. . | |
| 4,202,480 | 5/1980 | Annett . | |
| 4,256,251 | 3/1981 | Moshofsky . | |
| 4,296,881 | 10/1981 | Lee . | |
| 4,304,236 | 12/1981 | Conta et al. . | |
| 4,305,539 | 12/1981 | Korolkov et al. | 227/8 |
| 4,319,576 | 3/1982 | Rothfuss . | |
| 4,331,276 | 5/1982 | Bourque . | |
| 4,349,028 | 9/1982 | Green . | |
| 4,354,628 | 10/1982 | Green . | |
| 4,383,634 | 5/1983 | Green . | |
| 4,391,401 | 7/1983 | Moshofsky . | |
| 4,415,112 | 11/1983 | Green . | |
| 4,429,695 | 2/1984 | Green . | |
| 4,442,964 | 4/1984 | Becht | 227/8 |
| 4,473,077 | 9/1984 | Noiles et al. . | |
| 4,480,640 | 11/1984 | Becht . | |
| 4,500,025 | 2/1985 | Skwor . | |
| 4,506,670 | 3/1985 | Crossley . | |
| 4,508,253 | 4/1985 | Green . | |
| 4,519,532 | 5/1985 | Foslien | 227/8 |
| 4,520,817 | 6/1985 | Green . | |
| 4,523,695 | 6/1985 | Braun et al. . | |
| 4,527,724 | 7/1985 | Chow et al. . | |
| 4,530,453 | 7/1985 | Green . | |
| 4,540,110 | 9/1985 | Bent et al. . | |
| 4,556,058 | 12/1985 | Green . | |
| 4,568,009 | 2/1986 | Green . | |
| 4,569,346 | 2/1986 | Poirier . | |
| 4,576,165 | 3/1986 | Green et al. . | |
| 4,576,167 | 3/1986 | Noiles . | |
| 4,589,582 | 5/1986 | Bilotti . | |
| 4,591,085 | 5/1986 | DiGiovanni . | |
| 4,592,498 | 6/1986 | Braun et al. . | |
| 4,597,517 | 7/1986 | Wagdy . | |
| 4,605,004 | 8/1986 | DiGiovanni et al. . | |
| 4,606,344 | 8/1986 | Digiovanni . | |
| 4,606,345 | 8/1986 | Dorband et al. . | |
| 4,607,636 | 8/1986 | Kula et al. . | |
| 4,608,981 | 9/1986 | Rothfuss et al. . | |
| 4,612,933 | 9/1986 | Brinkerhoff et al. . | |
| 4,617,928 | 10/1986 | Alfranca . | |
| 4,633,861 | 1/1987 | Chow et al. . | |
| 4,633,874 | 1/1987 | Chow et al. . | |
| 4,646,745 | 3/1987 | Noiles . | |
| 4,664,305 | 5/1987 | Blake, III et al. . | |
| 4,665,916 | 5/1987 | Green . | |
| 4,684,051 | 8/1987 | Akopov et al. . | |
| 4,714,187 | 12/1987 | Green . | |
| 4,715,520 | 12/1987 | Roehr, Jr. et al. . | |
| 4,728,020 | 3/1988 | Green et al. . | |
| 4,741,336 | 5/1988 | Failla et al. . | |
| 4,807,628 | 2/1989 | Peters et al. . | |
| 4,809,898 | 3/1989 | Gassner et al. . | |
| 4,850,355 | 7/1989 | Brooks et al. . | |
| 4,863,088 | 9/1989 | Redmond et al. . | |
| 4,869,415 | 9/1989 | Fox . | |
| 4,881,544 | 11/1989 | Green et al. . | |
| 4,881,545 | 11/1989 | Issacs et al. . | |
| 4,892,244 | 1/1990 | Fox et al. . | |
| 4,915,100 | 4/1990 | Green . | |
| 4,938,408 | 7/1990 | Bedi et al. . | |
| 4,941,623 | 7/1990 | Pruitt . | |
| 4,955,959 | 9/1990 | Tompkins et al. . | |
| 5,031,814 | 7/1991 | Tompkins et al. . | |
| 5,040,715 | 8/1991 | Green et al. . | |
| 5,065,929 | 11/1991 | Schulze et al. . | |
| 5,071,052 | 12/1991 | Rodak et al. | 227/19 |
| 5,074,454 | 12/1991 | Peters . | |
| 5,083,695 | 1/1992 | Foslien et al. . | |
| 5,100,042 | 3/1992 | Gravener et al. . | |
| 5,106,008 | 4/1992 | Tompkins et al. . | |
| 5,129,570 | 7/1992 | Schulze et al. . | |

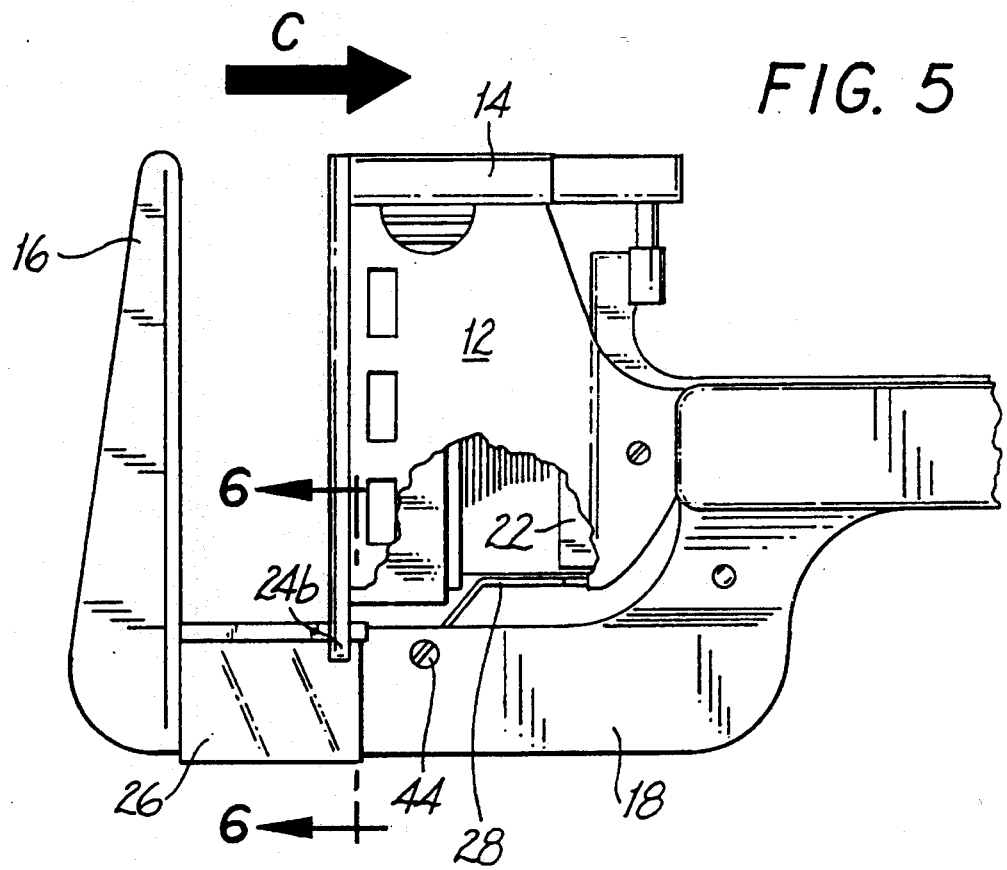
FIG. 5
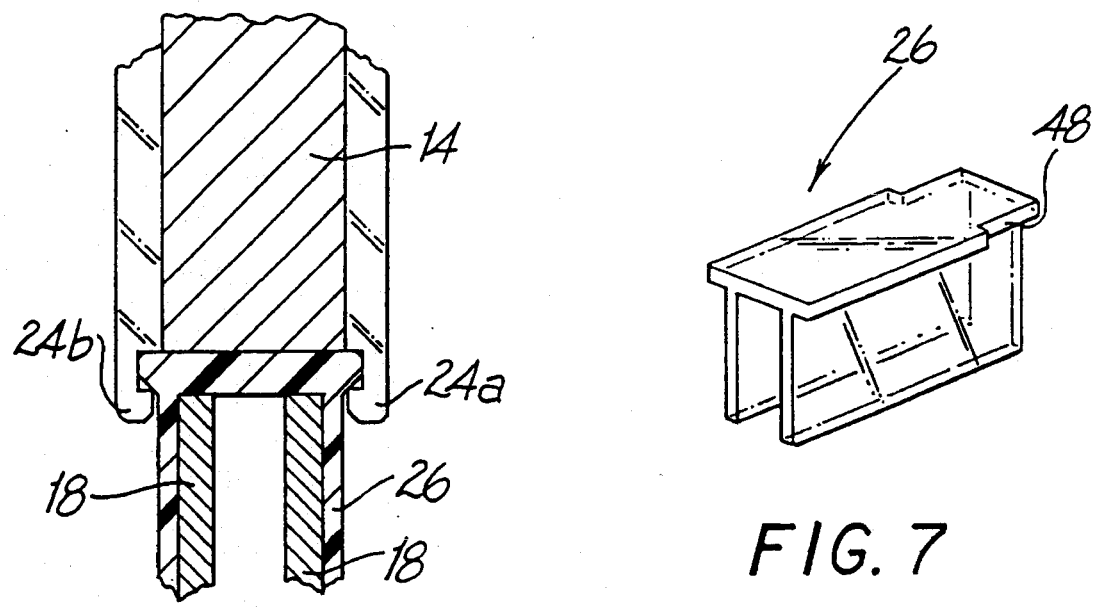
FIG. 6
FIG. 7

LOCKING DEVICE FOR AN APPARATUS FOR APPLYING SURGICAL FASTENERS

This is a continuation of application Ser. No. 08/275,227, filed on Jul. 14, 1994 now abandoned which is a continuation of application Ser. No. 8/071,935 filed on Jun. 3, 1993, now abandoned, which is a continuation of application Ser. No. 07/780,861 filed on Oct. 18, 1991, now abandoned.

BACKGROUND OF THE INVENTION

1. Field of the Invention

The present invention relates to devices for applying surgical fasteners, and more particularly to a locking mechanism for preventing premature or repeated firing of the surgical fastening apparatus.

2. Background of the Prior Art

Surgical fastening devices for simultaneously applying an array of surgical staples or other types of fasteners are known in the art. Such devices are used for suturing body tissue such as, for example, intestinal and gastric walls with spaced parallel rows of longitudinally aligned stapes. These surgical stapling devices reduce the time of wound closure in a surgical procedure.

Typically, these devices include a fastener cartridge disposed on one side of the tissue to be fastened, and an anvil assembly parallel to the fastener holder on the other side of the tissue to be fastened. The fastener cartridge is moved linearly towards the anvil assembly so that the tissue is clamped between them. The fasteners are driven from the fastener cartridge so that the ends of the fasteners pass through the tissue and are form finished as they make contact with the anvil assembly, thereby producing an array of finished fasteners in the tissue. Optionally, the fastening apparatus may include a knife mechanism for creating an incision between rows of fasteners. The fasteners can be made of metal, non-absorbable polymers, or bioabsorbable polymers such as polyglycolide, polylactide, and copolymers thereof. In addition, the anvil surface may support a plurality of retainers for cooperatively engaging the fasteners after the fasteners pass through the tissue.

In common use are devices in which the fastener cartridge comprises a disposable cartridge removably mounted on a cartridge jaw for supporting and actuating the cartridge. The cartridge is disposable after a single use, i.e. after the fasteners are fired. The fastener device is reusable after reloading with a fresh cartridge, and is generally reusable in a subsequent surgical procedure after cleaning, sterilizing, and reloading. Also known in the art are disposable surgical fastener devices, in which the entire apparatus is disposed of after a single use. Examples of such surgical fastening devices may be found in, among others, Green (U.S. Pat. No. 4,354,628), Green (U.S. Pat. No. 4,665,916), and Green (U.S. Pat. No. 4,568,009).

In the use of surgical fastener devices the possibility arises that the fastener device may be actuated when the cartridge is empty of staples or fasteners. This can occur when the apparatus has been fired once, but the cartridge has not been reloaded or discarded, and may also occur if the apparatus is inadvertently reloaded with a spent cartridge. Under such circumstances the fastening device will fail to suture the body tissue, which can cause harm to the patient due to the surgeon's loss of valuable time. The risk of harm is greatly increased if the apparatus contains a knife mechanism, since it will create an unsealed incision.

To eliminate these dangers to the patient it would be beneficial to provide a device which alerts the surgeon that a new cartridge is required. It would further be beneficial if such a device provides a locking mechanism to actually prevent the surgeon from trying to fire a cartridge that has already been fired and prevent approximation of the jaws should a spent cartridge be loaded into the cartridge jaw. This would save valuable time and reduce the risks to the patient.

Applications Ser. No. 07/936,884 filed Aug. 27, 1992 which is a continuation of Ser. No. 07/622,856 fled Dec. 6, 1990, now abandoned, and Ser. No. 07/928,700 filed Aug. 11, 1992, which is a continuation of Ser. No. 07/704,050 filed May 22, 1991, now abandoned, which is a continuation-in-part of Ser. No. 07/622,856 filed Dec. 6, 1990, now abandoned, disclose a mechanism for applying a plurality of surgical fasteners to body tissue. The devices further provide a locking mechanism for preventing the reapproximation of the jaw members and thus re-firing of the apparatus after a cartridge is spent (i.e. the fasteners have been fired) and the cartridge jaw is withdrawn from the anvil jaw. The locking mechanism disclosed therein is constructed as part of the cartridge, and moreover, the locking mechanism is at least partially located inside of the cartridge.

While this development represented an advance in the surgical fastener art, it is further desirable to provide a locking device that is part of the jaw mechanism of a surgical fastening device in contrast to part of a cartridge that will prevent the re-approximation of a spent cartridge. A locking device that is part of a frame or jaw mechanism relieves a fastener cartridge from cumbersome locking mechanisms, and further, since the locking mechanism will not be disposed of with the cartridge when the cartridge is spent, there is a corresponding reduction in cost in assembly and manufacture.

SUMMARY OF THE INVENTION

The present invention provides a surgical fastening apparatus for applying a plurality of surgical fasteners to body tissue which includes means for advancing a first jaw member towards a second jaw member to grip tissue therebetween prior to driving the fasteners into tissue. The apparatus further includes a locking device for preventing the advancing means from moving the first jaw member towards the second jaw member in the event a spent cartridge is held in the cartridge jaw. The locking device is positionable on the frame adjacent the second jaw member and is pivotable away from a cartridge containing a plurality of fasteners. When the fasteners are fired, the locking device pivots upwardly into an area defined by the jaw member and vacated by the fastener drivers. As the handle mechanism is released, the cartridge jaw moves to its non-advanced (retracted) position, pivoting the locking device temporarily downwardly as it passes over the locking device. The locking device then pivots back upwardly to engage a surface of the cartridge jaw, so that the first jaw member is thus prevented from advancing until a new cartridge is positioned for use in the apparatus. The positioning of the locking device adjacent the second jaw member on the frame provides a means for preventing premature advancement of the first jaw member, and allows for use of a cartridge including the plurality of fasteners without a locking device integral with the cartridge.

BRIEF DESCRIPTION OF THE DRAWINGS

The foregoing features of the present invention will become more readily apparent and may be understood by referring to the following detailed description of an illustrative embodiment of the locking device for use with a surgical fastening device of the present invention, taken in conjunction with the accompanying drawings, in which:

FIG. 5 is a side elevational view in partial cut away illustrating the engaged locking device preventing advancement of the cartridge jaw of the surgical fastening apparatus of FIGS. 3 and 4;

FIG. 6 is a cross-sectional view of the jaw mechanism shown in FIG. 5 taken along line 6—6;

FIG. 7 is a perspective view illustrating the guide track portion of the jaw mechanism of a surgical fastening apparatus;

DETAILED DESCRIPTION OF THE PREFERRED EMBODIMENTS

Figure 1:
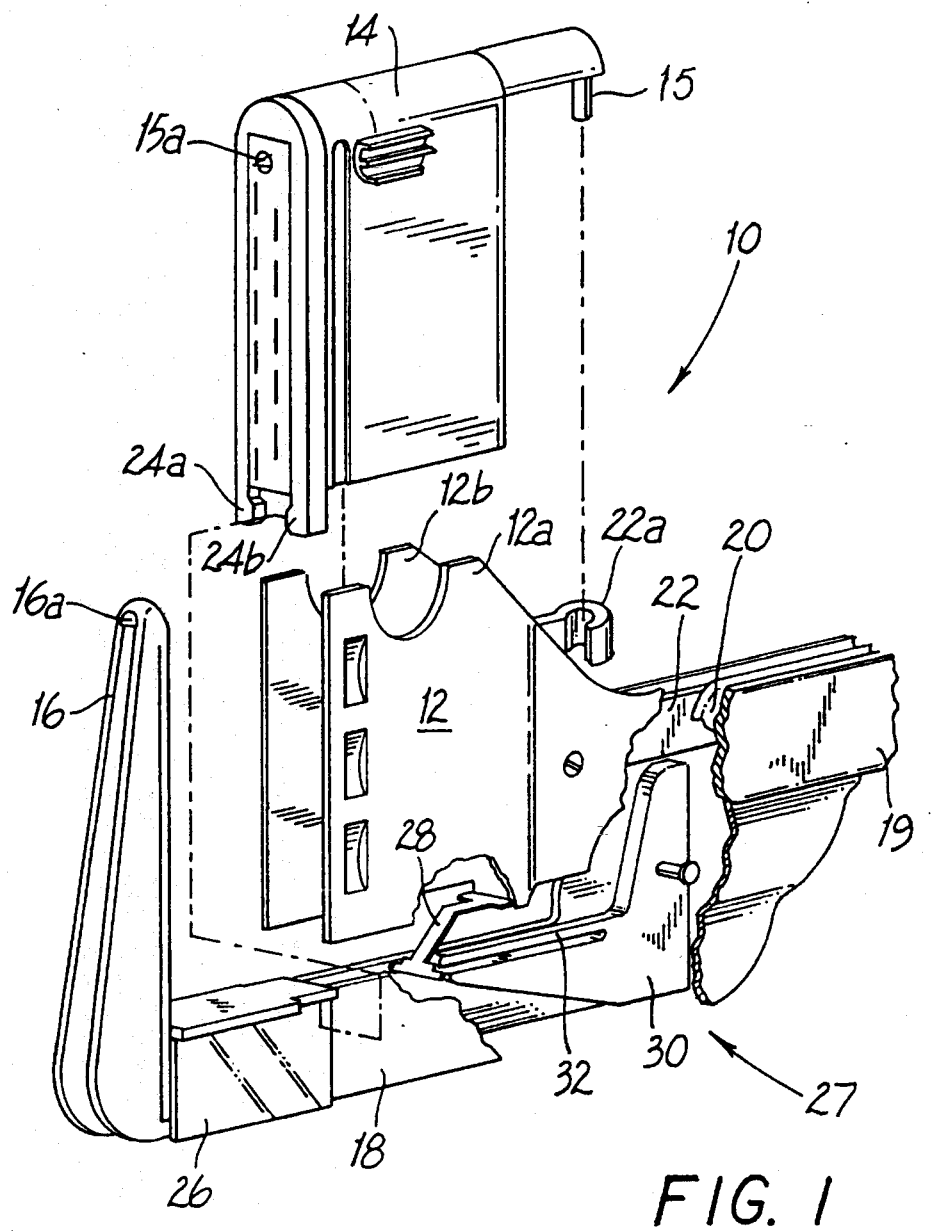
FIG. 1 is an exploded perspective view with a partial cut away view illustrating a cartridge end of a jaw mechanism of a surgical fastening apparatus having the locking device according to a first embodiment of the present invention.

Referring now in specific detail to the drawings, in which like reference numerals identify similar or identical elements throughout the several views, there is shown a jaw mechanism 10 having a locking device 27 which discourages or prevents the jaw mechanism 10 from becoming approximated into firing position when fasteners are not present in a cartridge 14.

Figure 2:
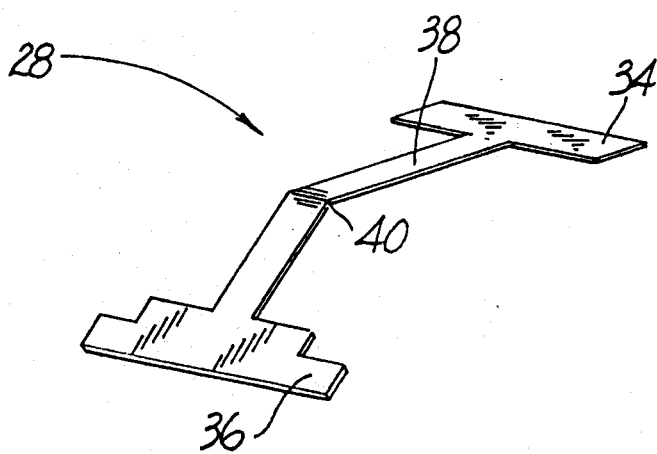
FIG. 2. is a perspective view illustrating a locking device according to a first embodiment of the present invention.

A first embodiment of the locking device 27 used in a jaw mechanism 10 of a surgical fastening apparatus is shown in FIGS. 1 and 2 of the drawings. The jaw mechanism 10 of the surgical fastening apparatus includes a cartridge jaw member 12 designed and configured to accept a fastener cartridge 14 between jaw arms 12a and 12b. Cartridge 14 includes a plurality of fasteners and is provided with guide posts 24a and 24b which engage guide track 26 on frame portion 18. Cartridge 14 further includes alignment pin 15 which will be described below. The proximal end of the first jaw member 12 is coupled to an approximating advancement member 22. An anvil jaw member 16 includes an anvil portion integral with a U-shaped frame portion 18. The proximal end of the U-shaped frame portion 18 is coupled to a body portion 19 of the surgical fastening apparatus.

Figure 3:
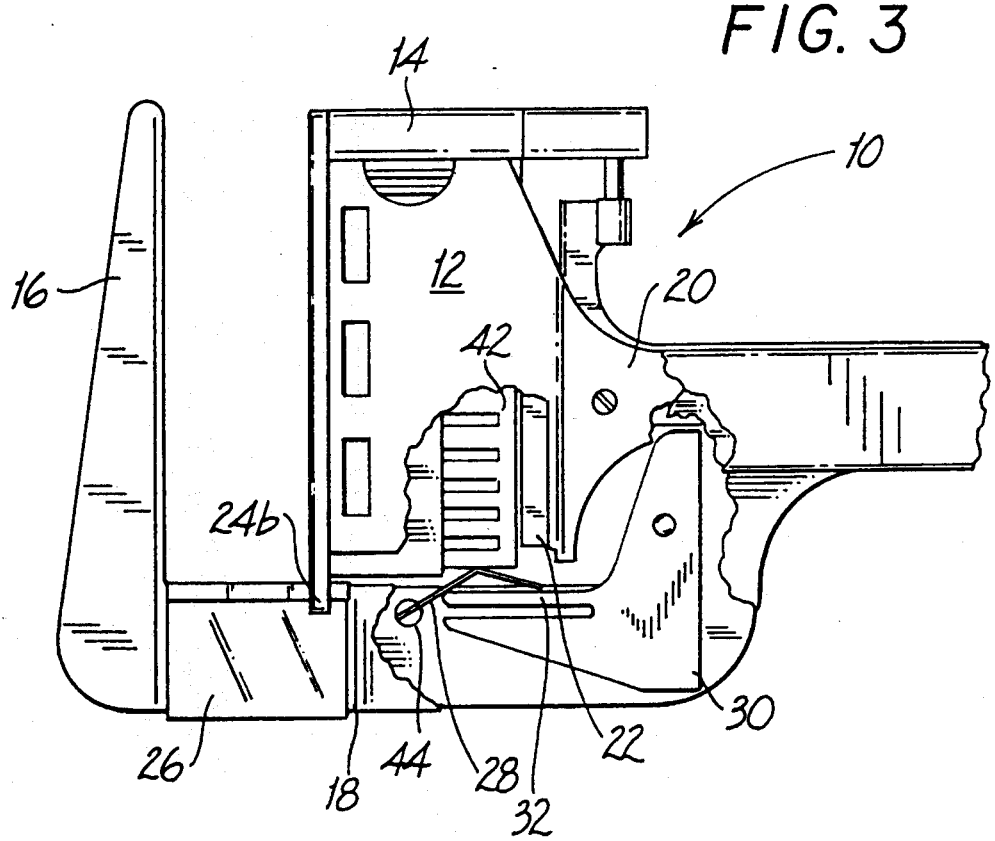
FIG. 3 is a side elevational view in partial cut away illustrating the locking device according to the first embodiment of the present invention in a non-engaged position prior to firing of the fasteners.

A locking device 27 is pivotably attached to the U-shaped portion 18 as shown and includes locking member 28 and support member 30. Support member 30 includes spring arm 32 which biases locking member 28 upwardly into an engaged position. Locking member 28 is a generally H-shaped member, as seen in FIG. 2, having a laterally extending abutment portion 34. The locking member 28 further includes a longitudinally extending body portion 38 having an articulation or bend 40 and a stepped laterally extending distal pivot post 36. The stepped distal post 36 is coupled to the U-shaped frame portion 18 at pivot point 44 (FIG. 3). The locking device is constructed of a resilient material, and is pivoted upward by spring arm 32 of support member 30 when coupled to the U-shaped portion 18 to engage the underside of the cartridge 14 having the plurality of fasteners situated therein.

In use, the jaw mechanism 10 is operable following positioning body tissue between the fastener cartridge 14 and the anvil jaw 16 by actuating a handle mechanism and approximating mechanism to urge approximating member 20 distally, so that cartridge jaw 12 is pushed towards anvil jaw 16 to position the body tissue between cartridge jaw 12 and anvil jaw 16. Alignment pin 15 is engaged in coupling arm 22a of advancement member 22 and is moved distally which cartridge jaw 12. When the tissue is held between cartridge jaw 12 and anvil jaw 16, pin 15 extends at point 15a through aperture 16a in anvil jaw 16 to prevent the tissue from extending beyond the jaw members. After the surgical fasteners are driven into the tissue and the staple legs are crimped by the anvil jaw 16, the apparatus is returned to its rest position by releasing the handle mechanism and the approximating member 20 is moved proximally with cartridge jaw 12, away from anvil jaw 16, thereby releasing the body tissue.

As shown in FIG. 3, the jaw mechanism 10 is in an at rest position. The fastener cartridge 14, holding a plurality of fasteners, is positioned in cartridge jaw 12. The locking member 28 abuts the underside of cartridge 14 at fastener drivers 42 and is pivoted downwardly out of engagement by drivers 42, against biasing spring arm 32 of support 30.

Figure 4:
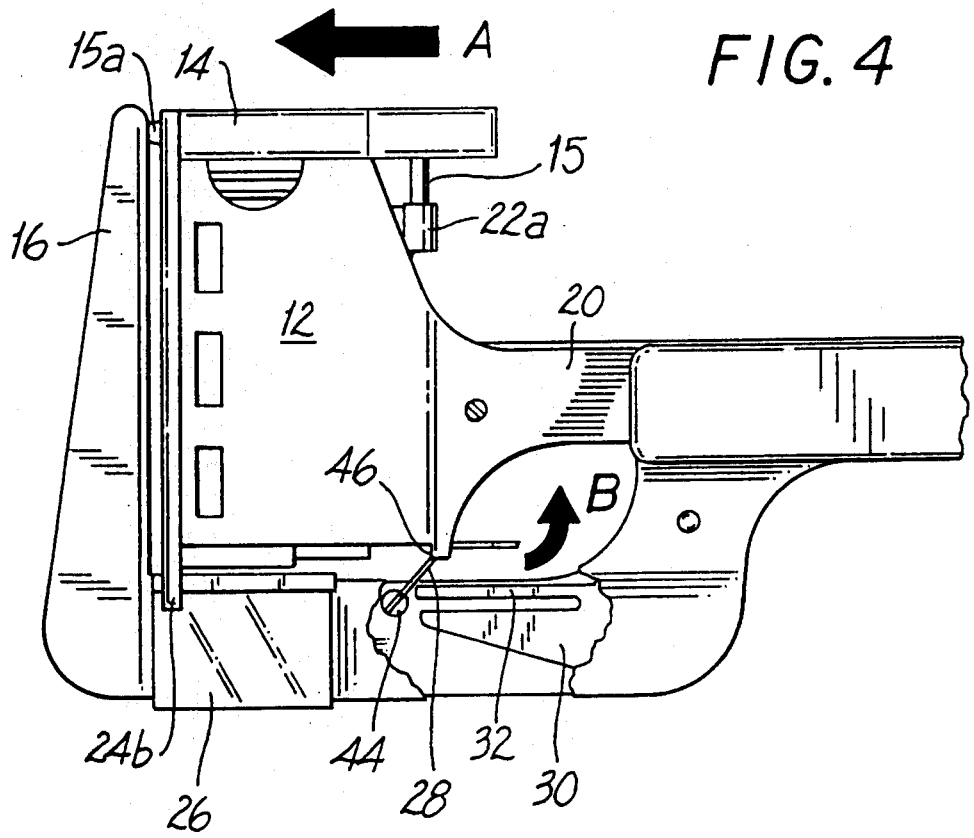
FIG. 4 is a side elevational view in partial cut away illustrating the locking device of FIG. 3 during firing of the fasteners.

Referring to FIG. 4, the jaw mechanism 10 is shown in an approximated position with the cartridge 14 adjacent anvil jaw 16. The jaw mechanism 10 is moved to this position by actuating an approximating mechanism to move approximating member 20 to forwardly advance cartridge jaw 12. A handle mechanism (not shown) is actuated to drive actuating member 22 through cartridge jaw 12 toward the distal end of the apparatus. Actuating member 22 drives fastener drivers 42 into the fasteners to force the fasteners into the tissue. After firing, the fastener drivers 42 remain in a distal position so the locking member 28 is allowed to be pivoted upwardly about pivot point 44 by spring arm 32 as shown into the interior space between jaw arms 12a and 12b so that bend 40 of body portion 38 is positioned between jaw arms 12a and 12b of jaw member 12.

As shown in FIG. 5, after the fasteners are applied to the tissue, jaw mechanism 10 is returned to the position of FIG. 3 by releasing the handle members and the approximating mechanism so that actuating member 22 and approximating member 20 move towards the proximal end of the apparatus. Locking member 28, resiliently extended upward between jaw arms 12a and 12b, is pivoted downwardly to allow cartridge jaw 12 to pass over it and then back upwardly to engage a notch 46 integral with the proximal end of cartridge jaw 12. Thus, the actuating member 22 and approximating member 20 cannot be driven distally to approximate cartridge jaw 12 towards anvil jaw 16 when the fasteners are not in the cartridge.

Referring to FIGS. 6 and 7, there is shown the guide track 26 of the U-shaped portion 18 upon which cartridge 14 rides. The guide track 26 of U-shaped portion 18 is designed to cooperate with guide posts 24a and 24b of cartridge 14 to properly align cartridge 14 during advancement and firing. Guide track 26 has a substantially T-shaped configuration and includes a stepped portion 48 to facilitate loading of the cartridge 14 thereon.

The locking device of the present invention enables the apparatus to be fired only once in a single use, by preventing re-approximation of the cartridge after the fasteners have been fired and the jaw mechanism is retracted to its non-engaged position. The apparatus can be refired by substituting a new cartridge loaded with fasteners to pivot the locking device 28 out of engagement. If the jaw mechanism is mistakenly reloaded with a spent (already fired) cartridge, the locking device will prevent approximation of the cartridge, since the fastener drivers will not bias the locking member out of engagement with the cartridge jaw, and thereby not allow the instrument to be fired.

Figure 8:
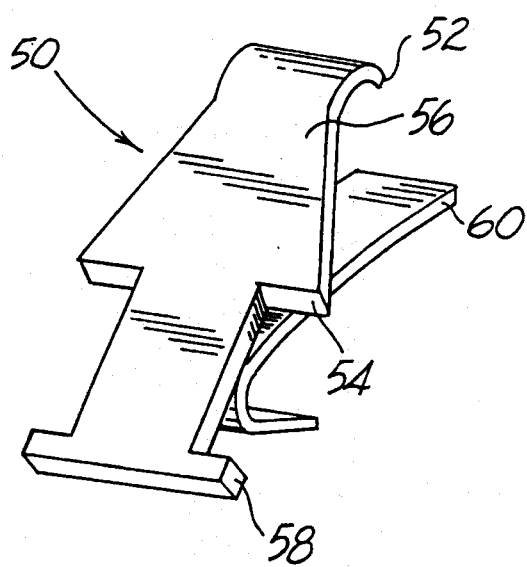
FIG. 8a perspective view illustrating a locking device according to a second embodiment of the present invention.
Figure 12:
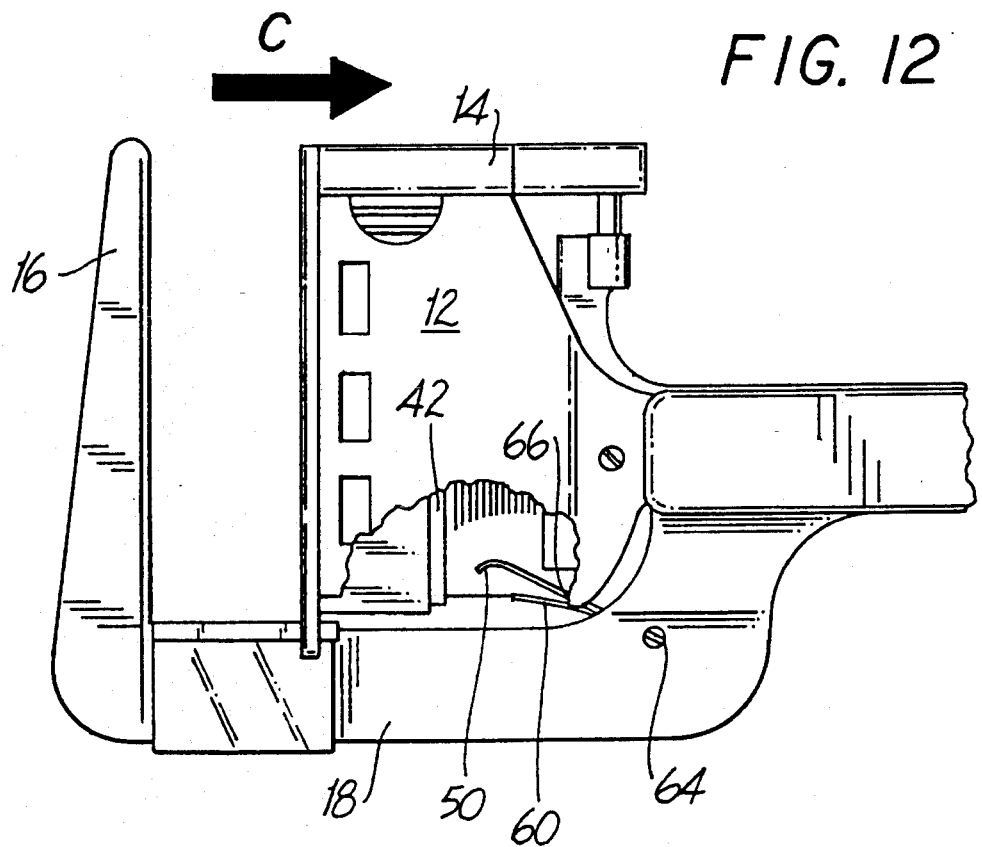
FIG. 12 is a side elevational view in partial cut away illustrating the engaged locking device of FIGS. 10 and 11 preventing advancement of the cartridge jaw.

Another embodiment of the locking member is shown in FIG. 8. Locking member 50 includes a generally triangular body portion 56 and a spring member 60 which is preferably, for example, spot welded to the triangular body portion 56. The triangular body portion 56 includes an abutment surface 54 at a mid-point for engaging notch 66 as best seen in FIG. 12. A laterally extending pivot post at a distal end is positionable at a proximal end of the jaw mechanism 10 in pivot point 64.

Figure 9:
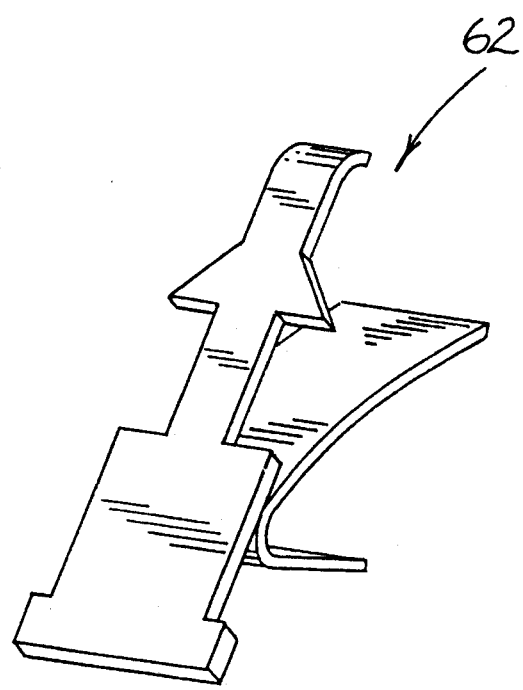
FIG. 9 is a perspective view illustrating a locking device according to a third embodiment of the present invention.

A further embodiment of the locking member is shown in FIG. 9. Locking member 62 is similar to locking member 50 above in construction as shown.

Figure 10:
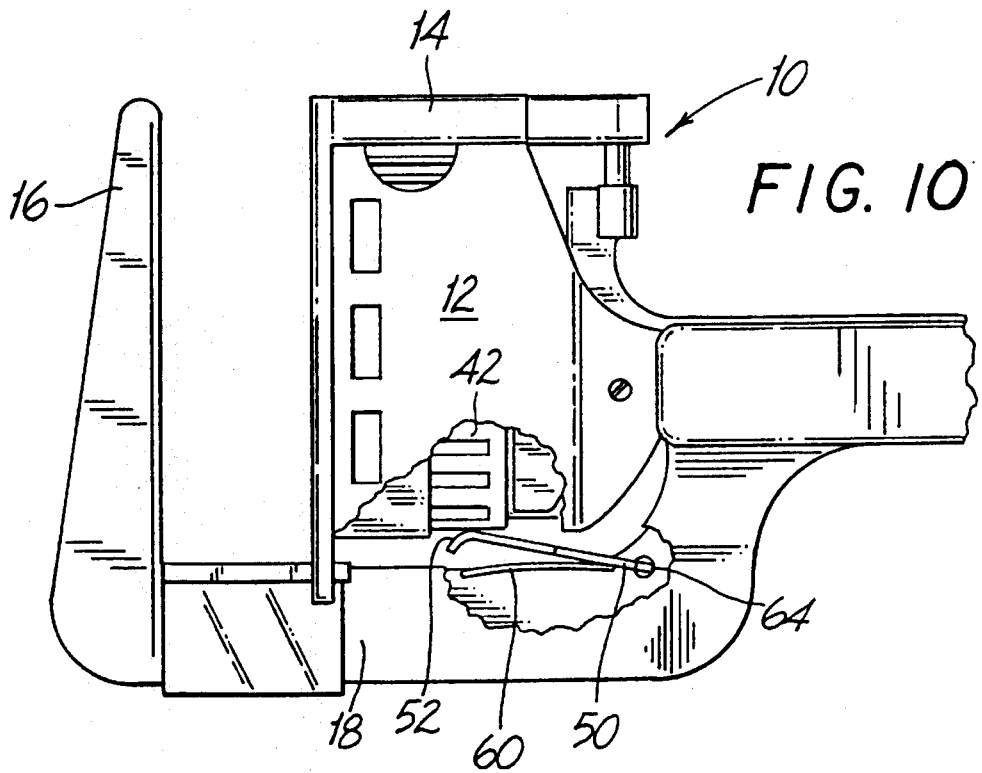
FIG. 10 is a side elevational view in partial cut away illustrating an alternate locking device positioned on a jaw mechanism in a non-engaged position of a surgical fastening apparatus according to a second embodiment of the present invention.
Figure 11:
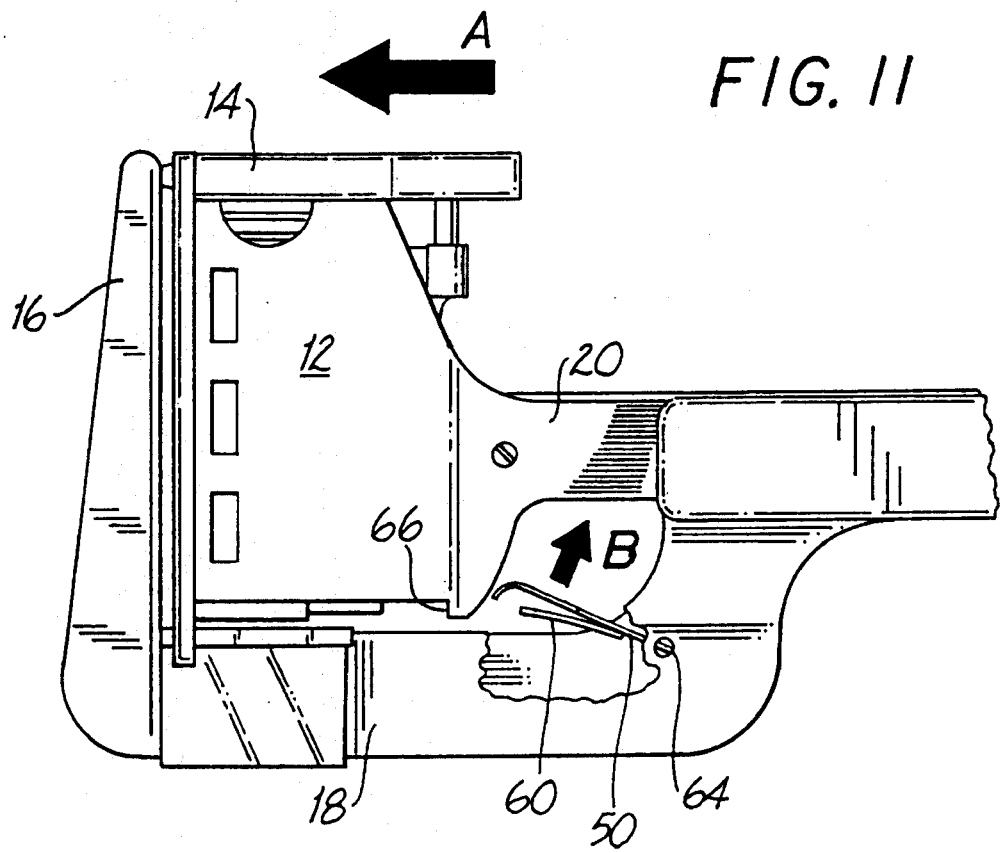
FIG. 11 is a side elevational view in partial cut away illustrating the locking device of FIG. 10 during firing of the fasteners.

Referring now to FIGS. 10–12, jaw mechanism 10 of the surgical fastening apparatus is shown incorporating either locking member 50 or 62. Jaw mechanism 10 includes cartridge jaw 12 and anvil jaw 16 as in the previous embodiment shown in FIGS. 1–7. However, in the embodiment shown in FIGS. 10–12, locking member 50 is pivotably attached to the proximal side of U-shaped portion 18 at pivot point 64. Spring portion 60 biases locking member 50 upwardly to engage the underside of cartridge 14 as shown in FIG. 10, which shows jaw mechanism 10 in an at rest position. Similar to FIGS. 4 and 5 discussed above, FIG. 11 shows the jaw mechanism 10 in an engaged position with locking device 50 resiliently extending upward following approximation of jaw members 12 and 16. Subsequent to firing the fasteners, the jaw mechanism 10 is moved proximally over locking member 50 to pivot member 50 downwardly and then upwardly to engage notch 66 and allow the body portion of locking member 50 to be positioned within the space defined by jaw arms 12a and 12b of cartridge jaw 12.

The term "fasteners" is used herein as a generic term which includes surgical staples, and the staple-shaped portion of two-part surgical fasteners, and equivalence thereof. It is further understood that the fasteners described herein are applicable to instruments for applying metal staples, as well as staples and two-part fasteners made from non-bioabsorbable or from bioabsorbable polymers (e.g. polyglycolide, polylactide and copolymers thereof).

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A locking device for a surgical fastener applying instrument, said instrument including a first jaw member having a cartridge containing a plurality of fasteners and a second jaw member, advancing means for approximating said first jaw member towards said second jaw member to grip tissue therebetween, and means for driving said fasteners from said cartridge into said tissue, said locking device comprising:

means for engaging said first jaw member, said engaging means positioned on said second jaw member and movable from a non-engaged position prior to said fasteners being driven from said cartridge to an engaged position subsequent to said fasteners having been driven from said cartridge, said engaging means including a cantilevered blocking portion for permitting proximal movement of said first jaw member subsequent to said fasteners having been driven from said cartridge and impeding distal movement of said first jaw member after said fasteners have been driven from said cartridge, said engaging means movable to said engaged position only after said fasteners have been driven from said cartridge.

2. A locking device according to claim 1, further comprising biasing means for pivoting said engaging means into said engaged position.

3. A locking device according to claim 2, wherein said biasing means comprises a leaf spring member coupled to said engaged means positioned in contact with said second jaw member to pivot said engaging means into said engaged position.

4. A locking device according to claim 2, further comprising a support member, said support member being secured to said second jaw member and including a spring arm for biasing said engaging means into said engaged position.

5. A locking device according to claim 1, wherein said cartridge containing said plurality of fasteners further contains a fastener driving member for driving said fasteners from said cartridge, said driving member contacting said engaging means to pivot said engaging means into said non-engaged position when said fasteners are contained within said cartridge.

6. A locking device according to claim 1, wherein said engaging means comprises a substantially H-shaped member, a first leg of said H-shaped member engaging said second jaw member to pivot said engaging means about an aperture in said second jaw member, and a second leg of said H-shaped member comprising a blocking member for engaging said advancing means to impede distal movement of said advancing means after said fasteners have been driven from said cartridge.

7. A locking device according to claim 6, wherein said H-shaped member includes a bend portion in a third leg connecting said first and second legs to cooperate with said second leg to engage said advancing means.

8. A locking device according to claim 1, wherein said second jaw member has a substantially U-shape portion, said engaging means being positioned on a base portion of said U-shape portion beneath said cartridge.

9. A locking device according to claim 1, wherein said second jaw member comprises a substantially U-shape portion, said engaging means being positioned on a proximal side of said U-shape portion adjacent a body portion of said surgical instrument.

10. A locking device according to claim 1, wherein said first jaw member comprises a pair of jaw arms having a slot therebetween for accepting said cartridge, said engaging means engaging said first jaw member between said arms after said fasteners have been driven from said cartridge.

11. A locking device according to claim 10, wherein said cartridge further comprises a fastener driving member, said engaging means engaging said driving member to pivot said engaging means to a non-engaged position when said cartridge contains said fasteners, and said engaging means pivoting to a position vacated by said driving member to engage said advancing means after said fasteners have been driven from said cartridge.

12. A locking device according to claim 1, wherein said engaging means engages said advancing means to prevent distal movement of said advancing means when said cartridge is removed from said first jaw member.

13. A locking device according to claim 1, further comprising cartridge guide means positioned on said second jaw member and engaging said cartridge to guide said cartridge into alignment with an anvil surface on said second jaw member.

14. A locking device according to claim 13, wherein said guide means comprises a T-shaped track member secured to said second jaw member cooperating with a complimentary shaped channel portion in said cartridge, said channel engaging said track member during approximation of said first jaw member.

15. A locking device according to claim 14, further comprising an alignment pin passing through said cartridge and engaging an aperture in said second jaw member, said pin being advanced during approximation of said jaw member by said advancing means.

16. In an apparatus for applying a plurality of surgical fasteners to body tissue, said apparatus including a first jaw member having a cartridge containing a plurality of fasteners positioned thereon and a second jaw member, advancing means for approximating said first jaw member towards said second jaw member to grip tissue therebetween, and means for driving said fasteners into said tissue; the improvement which comprises:

means positioned on said second jaw member for engaging said first jaw member, said engaging means moveable from a non-engaged position prior to said fasteners being driven from said cartridge to an engaged position subsequent to said fasteners having been driven from said cartridge, said engaging means including a cantilevered blocking portion for permitting proximal movement of said first jaw member subsequent to said fasteners having been driven from said cartridge and impeding distal movement of said first jaw member after said fasteners have been driven from said cartridge, said engaging means being disengaged from said first jaw member when said cartridge contains said plurality of fasteners and movable to said engaged position only after said fasteners have been driven from said cartridge.

17. An apparatus according to claim 16, further comprising biasing means for pivoting said engaging means into said engaged position.

18. An apparatus according to claim 17, wherein said biasing means comprises a leaf spring member coupled to said engaging means positioned in contact with said second jaw member to pivot said engaging means into said engaged position.

19. An apparatus according to claim 17, further comprising a support member, said support member being secured to said second jaw member and including a spring arm for biasing said engaging means into said engaged position.

20. An apparatus according to claim 16, wherein said cartridge containing said plurality of fasteners further contains a fastener driving member for driving said fasteners from said cartridge, said driving member contacting said engaging means to pivot said engaging means into said non-engaged position when said fasteners are contained within said cartridge.

21. An apparatus according to claim 16, wherein said engaging means comprises a leaf spring having a first leg for engaging said second jaw member to pivot said engaging means about an aperture in said second jaw member, and a second leg having an abutment portion for engaging said advancing means to impede distal movement of said advancing means and said first jaw member after said fasteners have been driven from said cartridge.

22. An apparatus according to claim 21, wherein said leaf spring includes a bend portion in said second leg to cooperate with said abutment portion to engage said advancing means and said first jaw member.

23. An apparatus according to claim 16, wherein said second jaw member has a substantially U-shape portion, said engaging means being positioned on a base portion of said U-shape portion beneath said cartridge.

24. An apparatus according to claim 21, wherein said second jaw member comprises a substantially U-shape portion, said engaging means being positioned on a proximal side of said U-shape portion of adjacent a body portion of said surgical instrument.

25. An apparatus according to claim 16, wherein said first jaw member comprises a pair of jaw arms having a slot therebetween for accepting said cartridge, said engaging means engaging said first jaw member between said arms after said fasteners have been driven from said cartridge.

26. An apparatus according to claim 25, wherein said cartridge further comprises a fastener driving member, said engaging means engaging said driving member to pivot said engaging means to a non-engaged position when said cartridge contains said fasteners, and said engaging means pivoting to a position vacated by said driving member to engage said advancing means and said first jaw member after said fasteners have been driven from said cartridge.

27. A surgical fastener applying instrument comprising:

a) a cartridge containing a plurality of surgical fasteners;

b) a jaw member adjacent the cartridge;

c) an advancement mechanism for moving the cartridge towards the jaw member to grip body tissue therebetween;

d) an actuation mechanism for driving the surgical fasteners from the cartridge for application to the body tissue; and e) a locking device having a first end pivotably mounted to the jaw member and a second deflectable end for engaging the advancement mechanism, the locking device being movable from a non-engaged position prior to the surgical fasteners being driven from the cartridge to an engaged position subsequent to the surgical fasteners having been driven from the cartridge to an inhibit movement of the cartridge towards the jaw member, the locking device moving to the engaged position only after the surgical fasteners have been driven from the cartridge.

28. A surgical fastener applying instrument as recited in claim 27, wherein said advancement mechanism further comprises a cartridge support member for supporting the cartridge, and a spring for biasing the deflectable end of the locking device into engagement with the cartridge support member.

29. A surgical fastener applying instrument as recited in claim 28, wherein the cartridge contains at least one fastener driver which inhibits the deflatable end of the locking device for engaging the cartridge support member prior to the surgical fasteners being driven from the cartridge.

* * * * *